(12) United States Patent
Bailey et al.

(10) Patent No.: US 7,823,829 B2
(45) Date of Patent: Nov. 2, 2010

(54) EQUIPMENT FASTENING DEVICE TO ENHANCE THE CRASH SAFETY OF AN AIRCRAFT

(75) Inventors: John Bailey, Duncan (CA); Bernhard Kobl, Tegernsee (DE); Jyrki Majamaeki, Unterhaching (DE)

(73) Assignee: Eurocopter Deutschland GmbH, Donauworth (DE)

(*) Notice: Subject to any disclaimer, the term of this patent is extended or adjusted under 35 U.S.C. 154(b) by 1092 days.

(21) Appl. No.: 11/470,337

(22) Filed: Sep. 6, 2006

(65) Prior Publication Data

US 2007/0063100 A1 Mar. 22, 2007

(30) Foreign Application Priority Data

Sep. 6, 2005 (DE) .................... 10 2005 042 400

(51) Int. Cl.
*B64C 1/20* (2006.01)
(52) U.S. Cl. ................................... 244/118.1
(58) Field of Classification Search ............. 244/118.1, 244/131, 119, 17.11; 24/704.1, 704.2; 188/371–377; 248/554, 557, 562, 573, 574
See application file for complete search history.

(56) References Cited

U.S. PATENT DOCUMENTS

| | | | | |
|---|---|---|---|---|
| 2,641,423 | A * | 6/1953 | Harriman et al. | 244/100 R |
| 3,444,962 | A * | 5/1969 | Lech | 188/371 |
| 6,224,104 | B1 * | 5/2001 | Hibino | 280/777 |
| 6,820,931 | B2 * | 11/2004 | Ruff et al. | 297/216.17 |
| 6,948,684 | B2 | 9/2005 | Beral et al. | |
| 2001/0002087 | A1 * | 5/2001 | Townsend | 280/801.1 |

FOREIGN PATENT DOCUMENTS

| | | |
|---|---|---|
| DE | 3827281 | 2/1990 |
| EP | 1197429 | 4/2002 |
| WO | WO-0246036 | 6/2002 |

OTHER PUBLICATIONS

Translation of German Office Action received in corresponding German Patent Application 10 2005 042 400.7-22.
W.G. Hienstorfer, "Crashstimuiationsrechnungen und Bauteilidealislerung für einen Luftfahrzeugunterboden" [Crash-simulation computations and component idealization for the subfloor of aircraft] published in the Zeitschrift for Flugwissenschaft und Weltraumforschung [magazine for aviation science and space research], vol. 11, 1987.

* cited by examiner

*Primary Examiner*—Timothy D Collins
*Assistant Examiner*—Michael Kreiner
(74) *Attorney, Agent, or Firm*—Young & Thompson

(57) ABSTRACT

An equipment-fastening device EFD to enhance the crash safety of aircraft, for fastening a piece of equipment to a support structure of an airframe, includes a load-limiting release mechanism and a load-peak transformer connected to the release mechanism and having a load-limiting, impact-energy-absorbing deformation element. Load peaks that occur in case of a crash and that stem from equipment fastened to the support structure by means of the equipment-fastening device are first reduced to a residual load peak by the EFD after the release, thereby relieving the stress on the support structure. Only then is any residual load peak that might still remain introduced via a first fastening section of the EFD into the support structure with a time delay vis-à-vis the load peaks that occurred originally.

8 Claims, 3 Drawing Sheets

EQUIPMENT FASTENING DEVICE TO ENHANCE THE CRASH SAFETY OF AN AIRCRAFT

Priority is claimed to German Patent Application No. 10 2005 042 400.7, filed on Sep. 6, 2005, the entire disclosure of which is incorporated by reference herein.

The present invention relates to an equipment-fastening device to enhance the crash safety of aircraft, as well as to an aircraft airframe having such an equipment-fastening device.

BACKGROUND

It is a known procedure to provide modern aircraft with constructions to enhance the crash safety which, in case the aircraft crashes or falls, reduce the risk of injury to passengers, flight crew and pilots is reduced and increase their chance of survival. To this end, such constructions are designed in such a way that, in case of a crash, they are deformed in a controlled manner, a process in which they absorb the highest possible amount of impact energy, and sufficiently absorb and limit impact loads. This, in turn, serves to reduce negative accelerations or load factors that occur in a crash, thus also reducing the loads that act on the above-mentioned occupants of the aircraft.

During a crash, especially rotary-wing aircraft such as, for example, helicopters, exhibit typical impact angles and impact velocities that can be predicted with quite good precision within a statistical framework. Moreover, the impact velocities are relatively low as a rule; they are often lower than those encountered in most vehicular accidents. For this reason, crash safety concepts are particularly promising for use with rotary-wing aircraft. Known airframe constructions that enhance the crash safety of helicopters employ shock-absorbing floor structures that are deformed in a controlled manner in case of a hard impact, so that this material deformation absorbs a large amount of the impact energy that is generated.

An airframe such as, for instance, the airframe of a rotary-wing aircraft or of a helicopter, has to be constructed so as to be not only high in strength but concurrently also very light in weight. These general requirements for lightweight construction mean that the airframe and its support structure can only be dimensioned for certain load factors or limit loads. The crash safety of the airframe is configured for these limit loads. When the airframe is designed, it has to be additionally taken into account that the area of the airframe that extends above the floor structure—which normally has a frame-like support structure with, for example, frame-shaped elements—encloses a cockpit or cabin area that is provided as a compartment for the aircraft occupants. Consequently, this frame-like support structure has to be designed so as to be especially stable and rigid in order to create a survival space for the aircraft occupants in case of a crash and also to prevent heavy components such as, for example, gears and/or rotors located above the airframe, from destroying this survival space.

If additional loads in the form of mobile pieces of equipment (for example, military backpacks for airborne troops) or permanently installed equipment (e.g. medical equipment, measuring devices, etc.) are attached to the support structure of the airframe, in case of a crash, these pieces of equipment generate large additional loads that are introduced into the support structure as high load peaks. This, however, means that the support structure, which also has to absorb the pulse-like loads stemming from the masses that are inherent to the aircraft in case of a crash, can become overloaded and fail. In other words, the crash safety of the airframe would no longer be ensured and the aircraft occupants would be greatly at risk.

In order to prevent this, the entire airframe would have to be designed to be so strong and stable right from the start that it can reliably absorb all of the additional loads and every load peak that occur. This, however, would translate into an extremely heavy construction, which runs fundamentally counter to the requirements for lightweight construction in aircraft. Especially in case of already existing airframe constructions, it would also be possible to retrofit the airframe structure with extra reinforcements. This measure, however, would likewise considerably increase the overall weight of the airframe. Moreover, such retrofitted reinforcements can only be realized with extremely high levels of technical expertise and skilled labor.

SUMMARY OF THE INVENTION

An object or technical problem of the invention is to provide a simple and effective equipment-fastening device to enhance the crash safety of aircraft, said device allowing a secure attachment of additional loads in the form of pieces of equipment to the support structure of an airframe without there being a need to additionally reinforce the support structure and without overloading the support structure in case of a crash, consequently reducing the risk of excessive deformation or destruction of the support structure in case of a crash; in this context, the equipment-fastening device should also be suitable for retrofitting existing airframe constructions. A further or alternate object is to provide an aircraft airframe with such an equipment-fastening device.

This equipment-fastening device to enhance the crash safety of aircraft, especially of a rotary-wing aircraft, comprises:

a first fastening section to which the device is to be fastened to a support structure;

a second fastening section to which a piece of equipment is to be fastened to the device;

a load-limiting release mechanism that defines a first load path between the first and second fastening sections, and which firmly joins the first and second fastening sections to each other below a pre-specified releasing force and which transmits a nominal load between the two fastening sections, said nominal load being smaller than the releasing force and stemming from the fastened equipment in the normal state (no crash), and which is released once the releasing force has been reached due to a crash and it severs the load-dissipating connection and the first load path between the first and second fastening sections; and a load-peak transformer having at least one load-limiting, impact-energy-absorbing deformation element that is connected to the first and second fastening sections and to the release mechanism, said deformation element forming a second load path between the first and second fastening sections after the release mechanism has been released and absorbing crash-induced load peaks that stem from the fastened equipment and that are greater than the releasing force, until a maximum possible nominal deformation is reached, and transmitting only part of the load peaks between the first and second fastening sections in a load-limiting manner, and transmitting a residual load peak between the first and second fastening sections, said residual load peak remaining due to the load-peak absorption once the maximum possible nominal deformation has been reached, whereby the residual load peak is introduced into the first fastening section with a time delay relative to the point in time when the release mechanism is released.

The equipment-fastening device according to the invention functions in two stages in case of a crash, each "stage" also having load-limiting properties or performing load-limiting functions. For this purpose, the device has two different load paths. The first stage is formed by the release mechanism through which the first load path runs until the crash-induced releasing force is reached, and through which the forces between the first and second fastening sections are dissipated until then. By being released at a pre-specified releasing force, the release mechanism prevents load peaks or overloads that exceed the magnitude of the releasing force from being introduced into the support structure to which the device is fastened. Therefore, the release mechanism has a load-limiting effect. The release mechanism can be released by a wide array of means. The release can be effectuated by the destruction of an element or else by means of non-destructive measures. A destructive release can be realized, for instance, by means of a predetermined breaking point or else by a part that snaps or tears away. Examples of the non-destructive release of a connection are a pre-tensioned connection against which the releasing force acts, latching connections, adhesive connections and the like.

The second stage is formed by the load-peak transformer (referred to below as LPT) through which the second load path also runs after the release mechanism has been released. After the release of the release mechanism, the LPT absorbs the impact energy that occurs in the form of load peaks during a crash and absorbs this impact energy through deformation or transforms it into deformation energy. This continues until the LPT has reached its maximum possible nominal deformation. During this deformation process, only some of the load peaks that occur are transmitted to the support structure by the LPT via the second load path. After all, the deformation causes a relatively large portion of the impact energy to be absorbed. Consequently, the forces exerted on the support structure are only relatively small. The LPT likewise has a load-limiting function in case of a crash, but it is not a pure load-limiting device since, once the maximum possible nominal deformation or the maximum deformation path has been reached, the LPT can still transmit a residual load to the support structure. This residual load is a residual load peak that could not be absorbed, or at least not completely, by the LPT during the load peak absorption. The LPT should preferably be configured in such a way that it displays a deformation force that is relatively small but as constant as possible along the entire deformation path as well as a very high tear resistance at the end of the deformation path.

In this manner, the residual load peak relative to the original crash-induced occurrence of load peaks that released the release mechanism is introduced into the support structure and thus into the airframe with a considerably time delay. Therefore, the LPT uncouples the global system "airframe" from the local system "LPT with equipment fastened to it", thus preventing the addition of load peaks within the support structure and within the airframe as a whole. During the time in which the LPT is deformed and absorbs impact energy, the support structure and the airframe as a whole are only subjected to a small load from the LPT and from the equipment fastened to it. At the same time, however, the airframe or an impact-absorbing floor structure that might be present in the airframe can absorb impact energy or load peaks caused by the mass of the airframe itself or by masses intrinsic to and arranged on the airframe due to the design of the system.

When, as a result of the load peak reduction brought about by the LPT and as a result of the load peak delay, the residual load peak is then introduced into the airframe, the airframe will already have dissipated its own load peaks through deformation of other airframe parts, especially the floor structure that lies underneath. This way, the load on the support structure of the airframe is considerably smaller and less critical than would be the case without the equipment-fastening device according to the invention.

Therefore, in case of a crash, the equipment-fastening device according to the invention allows a systematic influence of the course of the total load over time, thus achieving load peak control that leads to a considerable reduction of the total load on the airframe and especially to a decrease of the load on the support structures located above the floor structure as a result of the delay in the load peaks.

If equipment is mounted on the support structure of the airframe employing the equipment-fastening device according to the invention, the support structure does not have to be additionally reinforced within the scope of a pre-specified load factor range in order to ensure the same stability and crash safety that the airframe exhibits when such equipment has not been mounted onto it. Consequently, the stability and crash safety of the airframe are retained, even when heavy equipment is subsequently installed and, in many cases, these aspects can even be considerably improved.

Thus, the equipment-fastening device according to the invention allows additional loads in the form of equipment to be securely attached to the support structure of the airframe without a need for the support structure to be additionally reinforced or even rebuilt for this purpose. Moreover, the equipment-fastening device according to the invention can be configured in such a manner that it has a very flat design in its non-deformed initial state. This makes it possible to integrate the device into the available interior of an airframe in a very space-saving manner. Fundamentally speaking, however, the equipment-fastening device can also be employed outside of the airframe. Furthermore, the construction of the equipment-fastening device is relatively simple, which facilitates its production, and it does not weigh much, an aspect that is particularly advantageous for applications in aviation. Consequently, existing airframes can be easily retrofitted with the equipment-fastening device according to the invention without the need for complex modifications.

Thanks to the fact that the solution according to the invention combines load limitation, load peak absorption and load peak delay, it contributes to enhancing the crash properties of aircraft, especially of rotary-wing aircraft, as well as to increasing the safety of the aircraft occupants.

Additional preferred and advantageous embodiment features of the equipment-fastening device according to the invention are the subject matter of the claims.

The present invention also provides an airframe, especially a rotary-wing aircraft airframe, particularly a helicopter airframe, comprises:
  an impact-absorbing floor structure that constitutes a first impact-energy absorption device in case of a crash,
  an airframe area extending above the floor structure, especially a cabin area, having a frame-like support structure,
  at least one equipment-fastening device that is affixed to a section of the frame-like support structure located at the top relative to the floor structure and that constitutes a second impact-energy absorption device in case of a crash, which
  at first reduces to a residual load peak the load peaks that occur in case of a crash and that stem from equipment fastened to the support structure by means of the equipment-fastening device, thereby relieving the support structure, and then introduces the residual load peak into the support structure with a time delay vis-à-vis the load peaks that occurred originally, whereby the support structure then transmits the residual load peak to the floor structure.

As defined by the invention, an airframe encompasses not only a cockpit, a passenger cabin, a cargo hold and the like, but also other parts of the airframe or of the fuselage such as, for instance, the tail boom, hollow load-dissipating built-on parts, etc. The frame-alike support structure of the airframe, which can have frame-shaped or rib-like elements, is preferably rigidly joined to the floor structure.

With the airframe according to the invention, essentially the same advantages can be achieved as already explained above in conjunction with the equipment-fastening device according to the invention.

Additional preferred and advantageous embodiment features of the airframe according to the invention are the subject matter of the claims.

BRIEF DESCRIPTION OF THE DRAWINGS

Preferred embodiments of the invention with additional configuration details and further advantages will be described in greater detail and explained below making reference to the accompanying drawings, in which the following is shown.

DETAILED DESCRIPTION OF THE PREFERRED EMBODIMENTS

Figure 1:
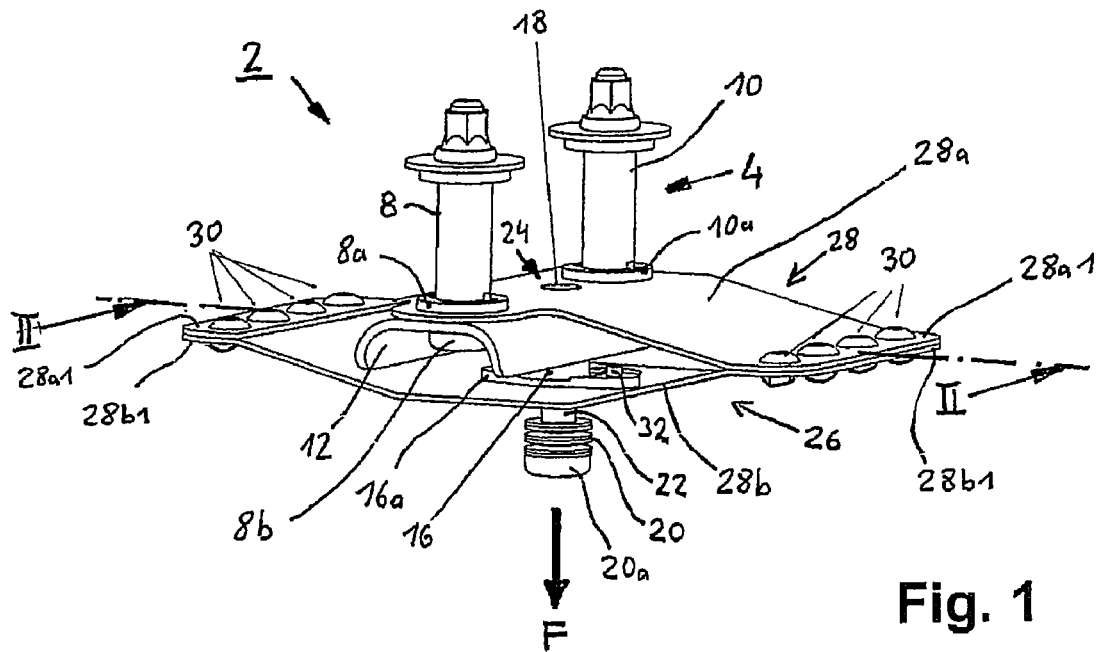
FIG. 1—a schematic perspective view of an equipment-fastening device according to the invention in a normal state (no crash)

In the following description and in the figures, for purposes of avoiding repetition, the same parts and components are also designated with the same reference numerals, insofar as no additional differentiation is necessary or practical.

Figure 2:
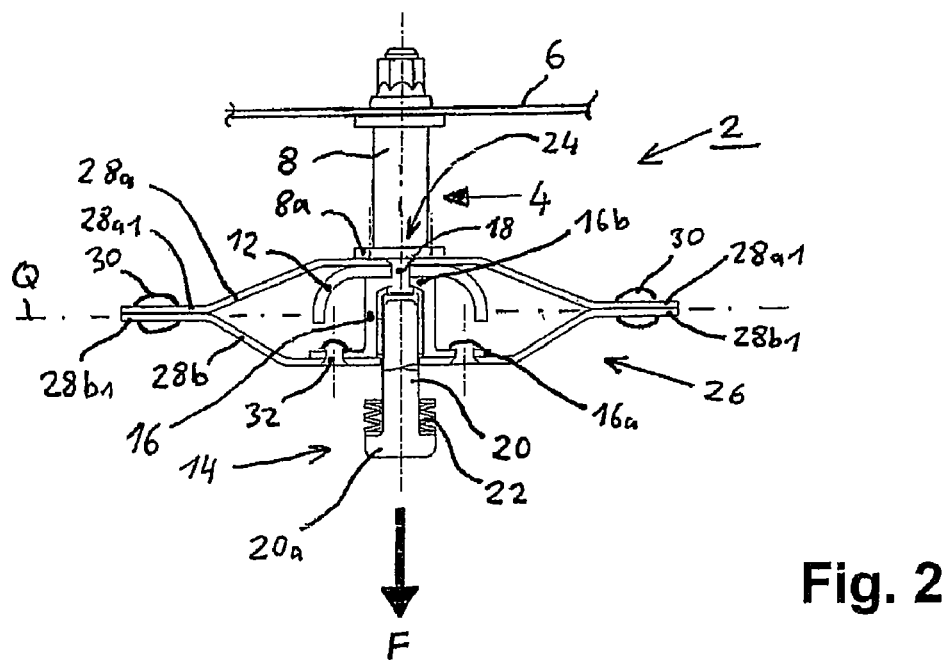
FIG. 2—a schematic sectional view of the equipment-fastening device from FIG. 1 along line II-II in FIG. 1.

FIG. 1 shows a schematic perspective view of an inventive, crash-safety-enhancing equipment-fastening device 2 (referred to below as EFD for short) in the normal state (no crash). FIG. 2 shows a schematic sectional view of the EFD 2 according to the invention from FIG. 1 along line II-II in FIG. 1.

The EFD 2 has a first fastening section 4 at which the EFD 2 is to be fastened to a support structure 6 (see FIG. 2) of an airframe (here, a helicopter airframe). In the present case, the first fastening section 4 comprises two fastening bolts 8, 10 at a distance from each other, by means of which the EFD 2 can be screwed onto the support structure 6. Instead of fastening bolts 8, 10, as a matter of principle, other suitable fastening elements could also be provided and the number of fastening elements can also be varied. It is even possible to configure the fastening element(s) as fixed, integral part(s) of the support structure 6 itself. The fastening bolts 8, 10 are affixed at their lower end to a reinforcement element which, in this example, is configured as a reinforcement rail 12 that has the approximate cross section shape of an inverted "U". As can be clearly seen in FIGS. 1 and 2, the edges or transitions of the U-shaped cross section to the side legs of the "U" are rounded off.

The EFD 2 also has a second fastening section 14 at which equipment or a piece of equipment (not shown here) is to be fastened to the EFD 2. The second fastening section 14 comprises a sleeve 16 having a hat-shaped cross section as well as a lower sleeve flange 16a. The sleeve 16 is joined at its sleeve cover 16b to the reinforcement rail 12 by means of a rivet 18. Moreover, the sleeve 16 has an internal thread, thus forming a sort of thread insert or a so-called helicoil insert. A section of a bolt-like holding element 20 having an external thread is screwed into this internal thread, and the piece of equipment (not shown here) can be connected to this holding element 20. For this purpose, the side of the holding element 20 facing away from the external thread has a bolt head 20a on which a spring element 22 is additionally mounted.

Relative to the lengthwise extension of the reinforcement rail 12 and relative to the distance of the two fastening bolts 8, 10 with respect to each other, the sleeve 16 and the holding element 20 screwed into it are located in a mid-section of the reinforcement rail 12 and arranged in an area between the fastening bolts 8, 10 (see FIG. 1). The second fastening section 14 and especially the holding element 20, however, are not limited to the above-mentioned embodiments, but rather, depending on the application case at hand, they can also have other suitable forms. Thus, for example, instead of the sleeve 16 and the bolt-like holding element 20, a one-piece holding unit can be created, or else the holding element can be configured as a hook, lug, eye, spring clip, snap closure, plug-in connector, coupling element or the like. By the same token, several of these elements can be provided, if necessary.

The EFD 2 also comprises a load-limiting release mechanism 24 that will be described in greater detail below and that, beyond the reinforcement rail 12, defines a first load path between the first and second fastening sections 4 and 14, that is to say, between the fastening bolts 8, 10 and the sleeve 16 and the holding element 20. Moreover, the EFD 2 is equipped with a load-peak transformer 26 (referred to below as LPT) having at least one load-limiting, impact-energy-absorbing deformation element 28 that is connected to the first and the second fastening section 4, 14 (in other words, here, the fastening bolts 8, 10, the sleeve 16 and the holding element 20) and the release mechanism 24.

The deformation element 28 in this example is configured as a bending element in the form of a hollow profile that has a wide, flattened profile cross section in the non-deformed state (no crash) depicted in FIGS. 1 and 2. The profile transverse axis Q of this flattened cross section that runs in the width direction of the EFD 2 extends essentially or almost at a right angle to a main load direction F that is to be expected in case of a crash. In this example, this main load direction F runs in the direction of the longitudinal axis of the fastening bolts 8, 10 and of the holding element 20 as indicated by a dot-dash line.

As can be seen in FIGS. 1 and 2, the flattened hollow profile of the deformation element 28 is made up of (at least) two parts (28a, 28b) shaped like strips or plates and arranged one above the other, whose side edges are securely joined to each other by means of joining elements (here, rivets 30). An extra reinforcement element (for example, a metal strip) can be arranged between a rivet head and each associated surface of the metal plates 28a, 28b, said reinforcement element preferably having rounded off edges on the side facing the bolts 8, 10. In the present case, two relatively thin metal plates, for example, steel plates, are employed as the strip-like or plate-like parts, and these plates are joined to each other at their side edges by means of rivets. The metal plates 28a, 28b have a rectangular contour.

In this example, the metal plates 28a, 28b each have the same thickness, which preferably lies in a range from about 1 mm to 3 mm. However, depending on the application case in question, the plate thickness can diverge from this value range and can be smaller or greater, as needed. Fundamentally speaking, the metal plates 28a, 28b can also be of different thicknesses. By the same token, the thickness of each metal plate 28a, 28b can vary locally and several layers of metal plates or locally varying numbers of layers can also be provided. In addition, the contour of the metal plates 28a, 28b can also be configured differently, especially in order to achieve certain bending properties. For instance, it is possible for halves of the metal plates 28a, 28b to the left and to the right of the longitudinal axis of the reinforcement rail 12 to have a trapezoidal, triangular, elliptical or other contour, including asymmetrical contours. If desired, the metal plates 28a, 28b can have free passage openings and/or indentations or notches.

The two metal plates 28a, 28b together form a flattened, essentially hexagonal hollow profile cross section with lateral edge webs 28a1, 28b1 lying one above the other, which are joined to each other by rivets 30. The metal plates 28a, 28b preferably have a high ductility and thus good plastic deformability with concurrent high tear resistance and a high elongation at break. The hollow deformation element 28 is not limited to the configuration described above. Instead of the at least two metal plates 28a, 28b, it would also be possible to use a one-piece hollow profile that is made, for example, by means of extrusion.

FIGS. 1 and 2 also show that the upper metal plate 28a is arranged symmetrically to the center axis of the EFD 2 as indicated by a vertical dot-dashed line in FIG. 2. Here, the upper metal plate 28a extends above the reinforcement rail 12 and is held between the latter and a collar 8a and 10a of an appertaining fastening bolt 8, 10. In this context, the appertaining fastening bolt 8, 10 extends through the upper metal plate 28a and through a center profile cross section of the reinforcement rail 12. This arrangement is held together by a bolt head 8b or 10b arranged underneath the reinforcement rail 12. This bolt head 8b, 10b can be produced, for example, by plastically deforming the lower end of the appertaining fastening bolt 8, 10.

The lower metal plate 28b, in turn, is arranged symmetrically to the center axis of the EFD 2 as indicated in FIG. 2 and joined at its top to the lower sleeve flange 16a by means of rivets 32 or other suitable fastening means. The holding element 20 can be screwed into the sleeve 16 through a bore in the lower metal plate 28b.

Thus, the fastening bolts 8, 10 of the first fastening section 4 engage with an upper, middle profile area of the hollow deformation element 28, while the sleeve 16, together with the holding element 20, which are associated with the second fastening section 14, engage with a lower, middle profile area of the hollow deformation element 28. In this construction, the sleeve 16 and the reinforcement rail 12 lie inside the hollow profile of the deformation element 28 that is formed by the two metal plates 28a, 28b.

In this embodiment, the above-mentioned release mechanism 24 is formed primarily by the sleeve cover 16b and the rivet 18 that joins the sleeve 16 to the reinforcement rail 12. In the normal operating state (no crash) and under normal operating loads (no crash), all of the forces stemming from the fastened equipment are borne by this rivet 18. In case of a crash, in contrast, the rivet 18 functions like a predetermined breaking point or trigger, as will be explained below. In this context, the desired releasing force of the release mechanism 24 can be pre-specified on the basis of the breaking strength or tear resistance of the rivet 18. The rivet 18 has a multiple function since, in the normal state (no crash), it not only functions as a load-dissipating element for the fastened equipment and as an additional connection between the upper metal plate 28a and the reinforcement rail 12, but also as a predetermined breaking point in case of a crash. Fundamentally, in the normal state, the rivet 18 could also join only the sleeve 16 and the reinforcement rail 12. The above-mentioned embodiment, however, is easier to produce from a manufacturing standpoint.

In the embodiment shown, the release mechanism 24 is arranged visibly inside the hollow profile of the deformation element 28. Generally speaking, however, the release mechanism 24 can also be placed outside of the deformation element 28 (for example, between several individual deformation elements arranged laterally next to each other), or at least partially inside the deformation element 28.

In the normal state (no crash) of the EFD 2 indicated in FIGS. 1 and 2, where the pre-specified release force has not been reached, the release mechanism 24 firmly joins the first and the second fastening sections 4, 14 to each other by means of the rivet 18. If a piece of equipment (not shown here) is fastened to the EFD 2 with the holding element 20, the above-mentioned first load path runs via the rivet 18, by means of which a nominal load that stems from the fastened equipment in the normal state (no crash) and that is smaller than the releasing force is transmitted between the holding element 20, the sleeve 16, the reinforcement rail 12, the upper metal plate 28a and the fastening bolts 8, 10.

Figure 3:
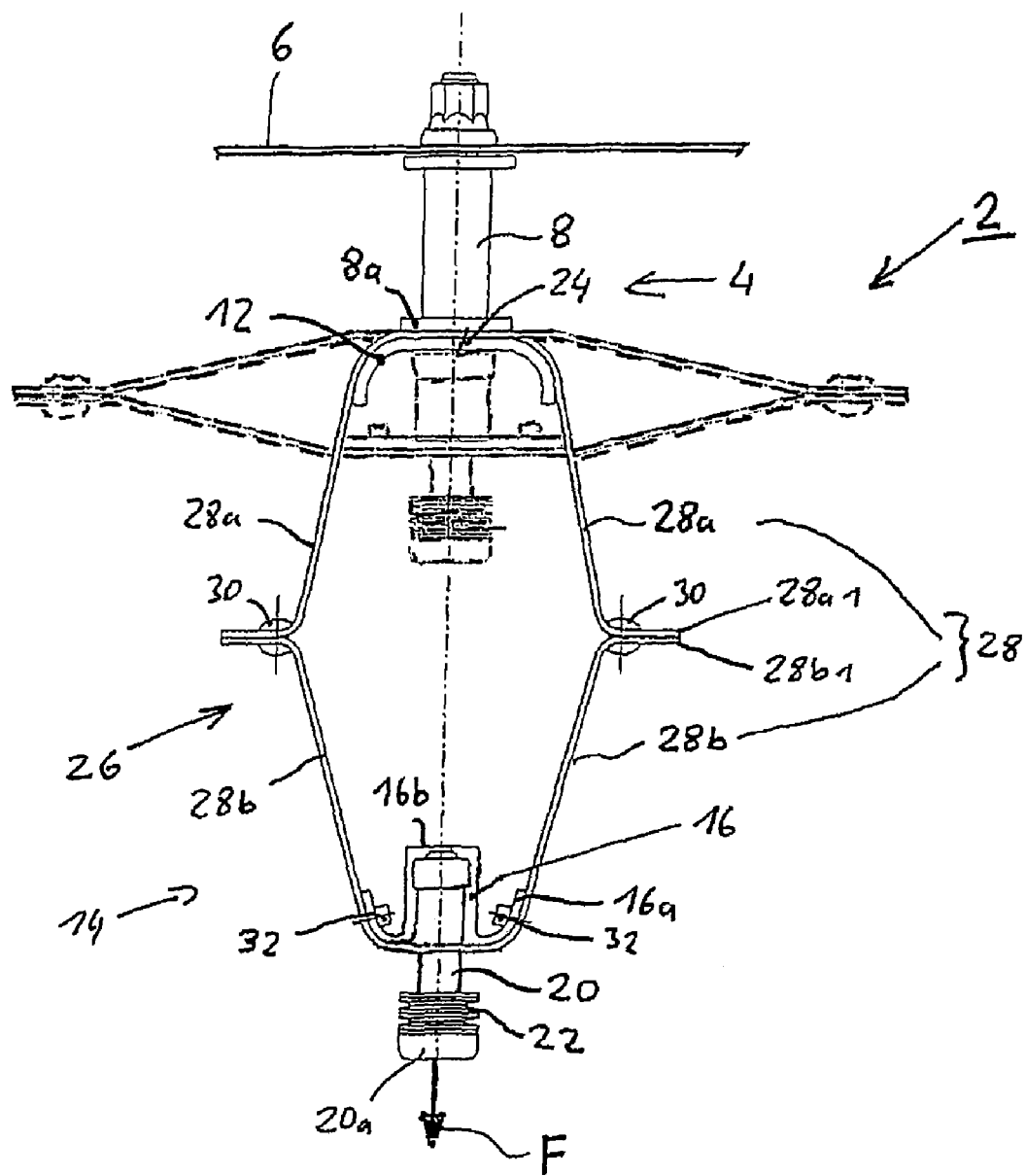
FIG. 3—a schematic front view of the equipment-fastening device from FIGS. 1 and 2 in case of a crash-induced deformation.

FIG. 3 schematically shows a front view of the EFD 2 from FIG. 1 and 2 with a crash-induced deformation and shortly before a maximum possible nominal deformation has been reached. For comparison purposes, the non-deformed initial state of the EFD 2 is indicated in FIG. 3 by broken lines. If, in case of a crash, the releasing force is reached or exceeded owing to the acceleration forces acting on the fastened equipment (not shown here), then the rivet 18 (see FIG. 2) that serves as the trigger breaks or snaps and the release mechanism 24 is released. The intentional failure of the rivet 18 severs the load-dissipating connection between the first and second fastening sections 4, 14 and the first load path. The arrangement then falls into the LPT 26. The breaking or snapping of the rivet 18 at a pre-specified breaking force concurrently has a load-limiting effect.

After the release, the forces that occur between the holding element 20 and the fastening bolts 8, 10 are now transmitted via the deformation element 28, which forms a new, second load path between the components of the first and second fastening sections 4, 14. Here, the force flows from the holding element 20 via the sleeve 16 into the lower metal plate 28b, via the rivet connection 30 into the upper metal plate 28a and from there via the reinforcement rail 12 into the fastening bolts 8, 10 and into the support structure 6. Due to the acceleration forces or impact loads in case of a crash, the holding element 20 is pulled away from its initial position, which lies in the immediate vicinity of the reinforcement rail 12, as shown in FIGS. 1 and 2. In this process, the two metal plates 28a, 28b, become bent or are bent open, changing from the shape depicted in FIGS. 1 and 2—which is a flattened hollow profile—into the shape shown in FIG. 3.

During this process, the upper metal plate 28a bends beyond the top of the reinforcement rail 12 and its rounded-off edges. In this manner, the forces that occur are distributed over a large surface area on the reinforcement rail 12 and prevent an undesired tearing of the metal plate 28a and consequently a premature failure. The largest bending deformations occur in those areas of the two metal plates 28a, 28b that lie in the vicinity of the rivet connection 30 as well as the sleeve 16 and the fastening rails 12. As can be seen in FIG. 3, the sleeve flange 16a is likewise bent in the process and consequently also acts as an additional deformation element along with its above-mentioned functions. The largest deformation of the sleeve flange 16a occurs at a relatively late deformation stage of the deformation element 28.

The deformation element 28 in this embodiment is configured as a tensile-deformation element. Also in case of a lateral force or acceleration component that might occur during the deformation process, said deformation element 28 will have a stabilizing effect and will even counteract lateral deformations. This constitutes a stable deformation behavior that increases the effectiveness of the EFD and also counteracts undesired impact-resilience properties.

The residual strength of the LPT 26 is selected in such a way that it is substantially greater than the deformation force needed to deform the deformation element 28. Even while the maximum possible nominal deformation of the deformation element 28 is being reached and after it has been reached, the EFD 2 will still be able to transmit considerable forces between the equipment (not shown here) fastened to the holding element 20 and the support structure 10 for a certain period of time before it or other adjacent parts or components fail.

In actual practice, the forces that act for a certain period of time on the equipment fastened by means of the EFD 2 in case of a crash are not uniform, but rather, constitute an irregular force course in the form of a sequence of varying load peaks.

Therefore, owing to the construction described above, the EFD 2 according to the invention functions as follows:

after the release mechanism 24 has been released, the crash-induced load peaks stemming from the fastened equipment—which are greater than the releasing force—and the associated impact energy from the load-limiting impact-energy-absorbing deformation element 28 of the LPT 26 are continuously absorbed until the maximum possible nominal deformation has been reached. In this process, the deformation element 28 that is being deformed consequently only transmits part of the forces caused by the load peaks between the first and second fastening sections 4, 14. During the deformation process, the limited forces that act on the support structure 6 are relatively constant; the result is an approximately constant force-path course. The reason for this is the above-mentioned configuration of the metal plates 28a, 28b and the plastic deformation they undergo during the bending process.

Once the deformation element 28 has reached its maximum possible nominal deformation, it then transmits a residual load peak that has remained due to the load-peak absorption between the first and second fastening sections 4, 14. This residual load peak is introduced into the first fastening section 4 and into the support structure 6 with a time delay relative to the point in time of the release of the release mechanism 24 (load-peak delay). As a function of the course of the crash as well as the magnitude and duration of the impact loads being exerted, due to the above-mentioned residual strength of the LPT 26, it can happen that the loads transmitted by the EFD 2 to the support structure 6 will continue to increase after the complete deformation of the deformation element 28 until the EFD 2 or a component connected to it fails. In any case, however, a considerable part of the damaging impact energy will have been absorbed by the EFD 2.

Figure 4:
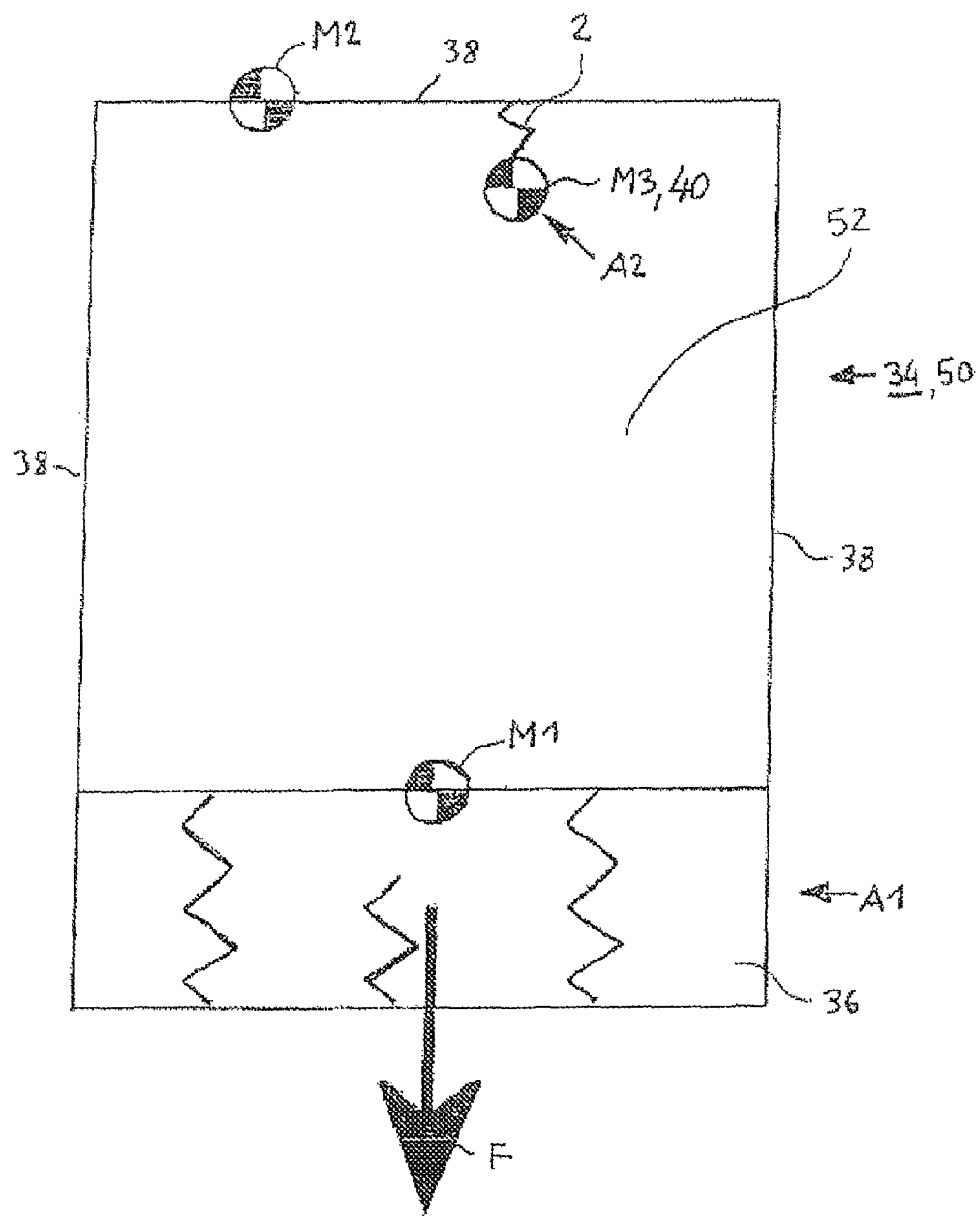
FIG. 4—a schematic, greatly simplified cross sectional view of a helicopter airframe according to the invention that is fitted with the equipment-fastening device according to the invention with which a piece of equipment is fastened to a frame-like support structure of the helicopter airframe.

FIG. 4 shows a schematic cross sectional view of an airframe of an aircraft 50 according to the invention that is fitted with an EFD 2 according to the invention. The airframe 50 here in this example is a helicopter airframe 34. The helicopter airframe 34 has an impact-absorbing floor structure 36 as well as an airframe area extending above the floor structure 36, said area comprising a cabin area 52, in this example, a helicopter cabin. The airframe area has a frame-like, frame-shaped or rib-like support structure 38 that is, for instance, integrally connected to the floor structure 36. This floor structure 36 forms a first impact-energy absorbing device A1 located below the helicopter cabin which, in case of a crash, defines a first deformation path for the helicopter airframe 34. The floor structure 36 is configured here in such a way that, in case of a crash and a resulting deformation, it exhibits a largely constant, uniform force-path course.

The helicopter airframe 34 is equipped with at least one equipment-fastening device (EFD) 2 that is affixed to a section of the frame-like support structure 38 located at the top relative to the floor structure 36. This upper section is a cover section of the frame-like support structure 38. However, side walls or side wall areas of the support structure 38 can also constitute such an upper section. A piece of equipment 40 is fastened to the support structure 38 by means of the EFD 2. In FIG. 4, the EFD 2 is indicated by a zigzag line.

Three masses M1, M2 and M3 are schematically drawn in FIG. 4. These masses are connected directly or indirectly to the helicopter airframe 34 and are statically and dynamically supported by the support structure 38. The reference numeral M1 stands for the mass of the helicopter cabin with its standard fixtures. The reference numeral M2 stands for the mass of the helicopter components arranged above the frame-like support structure 38 such as, for example, a drive, a rotor head and appertaining rotor blades. The reference numeral M3 stands for the mass of an additional load in the form of the piece of equipment 40 that is attached to the support structure 38 by means of the EFD 2. The arrow F stands for the main direction of load of the acceleration forces acting on this entire system in case of a vertical crash.

In case of a vertical fall of the helicopter, in other words, a vertical crash, the mass M1 acts directly on the first impact-energy-absorbing device A1, in other words, the impact-absorbing floor structure 36 of the helicopter.

The forces and impact pulses stemming from the mass M2 in case of a vertical crash are introduced via the frame-like support structure 38 into the first impact-energy-absorbing device A1. Therefore, this frame-like support structure 38, as an essential part of the cabin area, has to be designed so as to be particularly stable and rigid in order to create a survival space for the aircraft occupants in case of a crash and to protect them from the effects of the mass M2 located above the cabin. The frame-like support structure 38 is designed as a "non-deformable structure" in terms of the load factors and limit loads that are decisive for dimensioning the helicopter airframe 34, whereas the floor structure 36 is intentionally designed as a "deformable structure".

Consequently, in view of the pre-specified load and safety requirements, the frame-like support structure 38 would have to be dimensioned in such a way in terms of its stability that it would be able to introduce all of the forces or load peaks stemming from the mass M2 into the floor structure 36 and thus into the first impact-energy-absorbing device A1 without permanent damage. Thus, within the scope of a pre-specified load factor range, the stability and strength of the support structure 38 should be dimensioned for the largest possible load peaks that could still stem from the mass M2. At the same time, however, the frame-like support structure 38 is subject to a basic requirement that applies to every aircraft component, namely, that it should be as lightweight as possible. The contradictory requirements resulting from the need for the greatest possible strength combined with the lowest possible weight have to be taken into consideration by design engineers during the configuration of the helicopter airframe 34.

When certain missions require additional loads in the form of mobile pieces of equipment or permanently installed equipment (such as, for instance, medical devices, measuring instruments, inserts or add-ons for military purposes, etc.) to be subsequently attached to the frame-like support structure 38 of a finished helicopter, in case of a crash, this equipment generates additional loads—symbolized by the mass M3 in FIG. 4—that are introduced as high load peaks into the frame-like support structure 38. In case of a vertical crash, this can cause the maximum permissible load capacity of the frame-like support structure 38 and appertaining areas of the helicopter airframe 34 to be exceeded, especially causing the support structure 38 to fail or to fail prematurely. The desired crash safety of the helicopter airframe 34 would no longer be ensured.

In order to prevent this, the frame-like support structure 38 as well as other parts of the helicopter airframe 34 would have to be reinforced. Such a reinforcement, however, would not only be very demanding to produce, but would also result in an extremely heavy construction, as has already been elaborated upon in detail in the introduction to the description.

Since, in the helicopter airframe 34 according to the invention, the equipment 40 is fastened to the frame-like support structure 38 by means of at least one EFD 2, such an extra reinforcement of the support structure 38 is not necessary and an undesired increase in the weight of the entire construction can be avoided.

After all, in case of a vertical crash, the EFD 2 with its LPT functions as a second impact-energy-absorbing device A2 that first converts the kinetic energy stemming from the mass M3 of the appertaining piece of equipment 40 into deformation energy, that is to say, the occurring load peaks are reduced by the deformation of the metal plates down to a residual load peak. As a result, the load acting on the support structure 38 is limited and the support structure 38 is substantially unstressed. Only once the deformation process has been completed and the metal plates 28a, 28b (see, for example, FIG. 1) have reached their maximum possible nominal deformation is any residual load peak that might still be present introduced into the support structure 38 with a time delay relative to the load peaks that had occurred originally. The support structure 38 then transmits the residual load peak to the floor structure 36.

Therefore, with the solution according to the invention, the remaining impact energy or the residual load peaks, are only introduced into the support structure 38 at a point in time at which the load peaks caused by the mass M2 and introduced into the support structure 38 at the beginning of the crash have already been dissipated to a large extent by the first impact-energy-absorbing device A1. For this reason, the time-delayed introduction of the energy stemming from the mass M3 into the frame-like support structure 38 does not allow the maximum permissible load capacity to be exceeded.

In other words, with the helicopter airframe 34 according to the invention, the deformation path caused by the mass M3 of the fastened equipment 40 in case of a vertical crash is distributed over a global, first deformation of the floor structure 36 and over a local, second deformation of the EFD 2 to which the mass M3 has been fastened or from which it has been suspended. As a result, the frame-like support structure 38 that functions as a transmission element between the mass M3 and the floor structure 36 is exposed to the acceleration forces or loads stemming from the mass M3 with a time delay and only to a lesser extent, so that it is unstressed. Consequently, in case of a crash, this results in a kind of two-stage impact absorption and impact-load limitation. A detrimental load peak addition can thus be avoided.

The invention is not restricted to the embodiment described above. The equipment-fastening device (EFD) according to the invention and the airframe according to the invention can also have other suitable embodiments within the framework of the protective scope.

The deformation element can also be made of a material other than metal. Thus, in certain application cases, it is provided for the deformation element to be made of fiber-composite material. Mixed forms consisting of metal and of a fiber-composite material are also possible. If the deformation element is configured as a hollow profile, it can also have a shape different from the above-mentioned cross sectional shape. Instead of a hexagonal cross section, other polygonal cross sectional shapes as well as curved cross sections with convex and/or concave areas can also be realized. Mixed shapes are likewise conceivable. The deformation element does not necessarily have to be configured as a hollow profile. Thus, for instance, the deformation element can be made up of a meander-like or zigzag-like folded strip of material or sheet metal whose individual sections are tight in the non-deformed state and lie on each other without any interstices so as to give the impression of a solid block. This construction is then pulled apart during a deformation process. A configuration with interstices is likewise conceivable. The deformation element can also be constructed in such a way that the energy is not absorbed by a bending deformation, but rather, for example, through the compressing or squashing, stretching, shearing, expanding, etc. of a component. Mixed forms of the above-mentioned constructions are likewise feasible.

Moreover, the release mechanism can also be configured differently from the manner described above. Instead of using a component loaded by tensile forces, such as the above-mentioned rivet, it is also conceivable to use elements for the releasing that are loaded by compressive forces or tensile and compressive forces. Thus, for instance, it is conceivable that, for the release, a pin-like part is pulled through a bushing, expanding the latter due to expansion forces until the pin finally slides out or tears out of the expanded bushing, thus effectuating the release. Release elements loaded by pre-tensioning devices or even release mechanisms controlled by more complex sensors are likewise feasible.

If the EFD according to the invention is used to fasten large objects that require multiple fastening points, several EFDs can be employed for this purpose which have either the same properties or else different properties. Similarly configured EFDs can also be used whose release mechanisms are set to different releasing forces and/or whose LPTs exhibit different impact-absorption properties. This allows for a uniform loading of all of the EFDs, especially in the case of fastening points that are arranged at differing distances from the center of gravity of the piece of equipment to be fastened, so that in case of a crash, a tilting or rotating of the affixed piece of equipment is prevented.

The reference numerals in the claims, in the description and in the drawings serve merely to better elucidate the invention and should not be construed as limiting the scope of protection.

What is claimed is:

1. An equipment-fastening device for fastening a piece of equipment to a support structure of an aircraft, the equipment-fastening device comprising:
a first fastening section configured to fasten to the support structure;
a second fastening section configured to fasten to the piece of equipment;
a load-limiting release mechanism defining a first load path between the first and second fastening sections, the release mechanism joining the first and second fastening sections to each other at a load dissipating connection below a pre-specified releasing force and transmitting a nominal load between the first and second fastening sections, the nominal load being smaller than the releasing force and stemming from the piece of equipment in a normal non-crash state, wherein the release mechanism is released when the releasing force is reached due to a crash so as to sever the load-dissipating connection and so as to sever the first load path; and
a load-peak transformer connected to the first and second fastening sections and to the release mechanism, and having at least one load-limiting, impact-energy-absorbing deformation element configured as two deformable plates disposed one above the other and joined at each end with a space therebetween to form a hollow profile, the deformable plates providing a second load path between the first and second fastening sections after a release of the release mechanism and configured to absorb crash-induced load peaks stemming from the fastened equipment that are greater than the releasing force until a maximum possible nominal deformation of the load-peak transformer is reached, and to transmit only part of the load peaks between the first and second fastening sections in a load-limiting manner, and wherein the deformation element transmits a residual load peak between the first and second fastening sections, the residual load peak remaining due to the absorption of the load-peak after the maximum possible nominal deformation has been reached, the residual load peak being introduced into the first fastening section with a time delay relative to the release of the release mechanism.

2. The equipment-fastening device as recited in claim 1, wherein said hollow profile includes an upper, middle profile area and a lower, middle profile area, the first fastening section being disposed on the upper, middle profile area and the second fastening section being disposed on the lower, middle profile area.

3. The equipment-fastening device as recited in claim 2, wherein the hollow profile has a flattened profile cross section and a profile transverse axis extending essentially at a right angle to a main load direction in the normal non-crash state.

4. The equipment-fastening device as recited in claim 2, wherein the release mechanism is arranged inside the hollow profile.

5. The equipment-fastening device as recited in claim 2, further comprising a reinforcement element associated with the first fastening section disposed inside the hollow profile and connected to the first fastening section.

6. The equipment-fastening device as recited in claim 5, wherein the reinforcement element has rounded-off edges on a side facing the first fastening section, at least a partial area of the hollow profile bending beyond the rounded-off edges after the release of the release mechanism.

7. The equipment-fastening device as recited in claim 1, wherein the deformation element includes metal.

8. The equipment-fastening device as recited in claim 1, wherein the release mechanism has a predetermined breaking point that breaks when the releasing force is reached.

* * * * *